United States Patent [19]

Onsager et al.

[11] 4,045,500

[45] Aug. 30, 1977

[54] PREPARATION OF ETHYLENE GLYCOL

[75] Inventors: Olav T. Onsager, Suffern, N.Y.; Peter L. Szecsi, Montclair, N.J.

[73] Assignee: Halcon International, Inc., New York, N.Y.

[21] Appl. No.: 691,113

[22] Filed: May 28, 1976

[51] Int. Cl.[2] .................. C07C 29/02; C07C 47/06
[52] U.S. Cl. ......................... 260/635 H; 260/604 R
[58] Field of Search ............... 260/636, 635 H, 604 R

[56] References Cited

U.S. PATENT DOCUMENTS 3,928,474  12/1975  Witheford ................. 260/635 H

*Primary Examiner*—Joseph E. Evans
*Attorney, Agent, or Firm*—William C. Long; David Dick; Riggs T. Stewart

[57] ABSTRACT

Ethylene glycol is prepared in an oxidation zone by the reaction of ethylene, molecular oxygen, and water in the presence of an iodine source to produce a liquid reaction product which is separated into a lower-boiling portion, a glycol fraction and a higher-boiling portion and the higher-boiling portion is recycled to the oxidation zone together with part of the lower-boiling portion.

4 Claims, 1 Drawing Figure

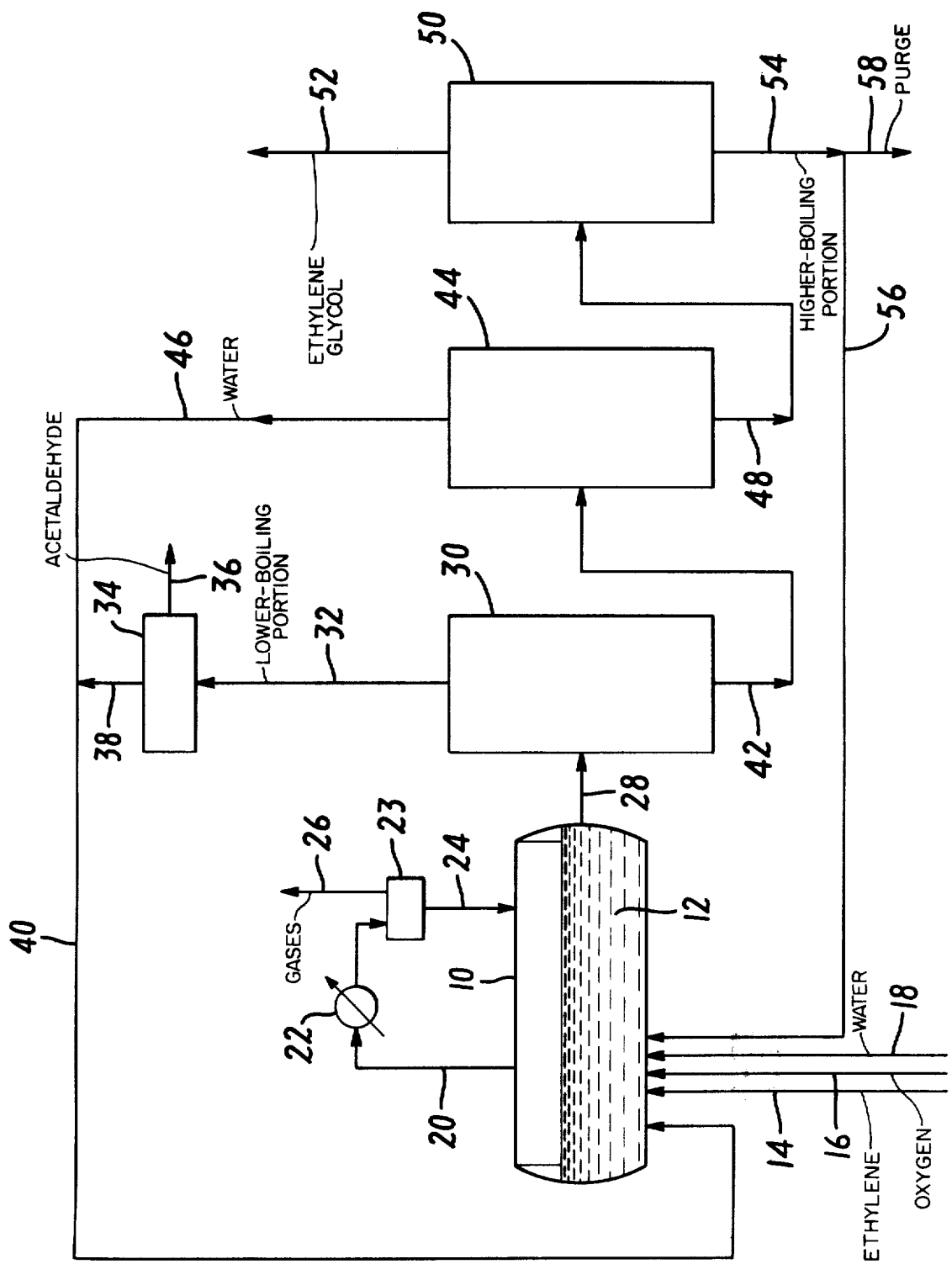

PREPARATION OF ETHYLENE GLYCOL

This invention relates to the preparation of ethylene glycol, and is more particularly concerned with a process for directly producing ethylene glycol by the molecular oxygen oxidation of ethylene in the presence of water and in the presence of iodine or an iodine-liberating compound as a catalyst.

Ethylene glycol is a chemical of acknowledged commercial importance and it is used, for example, in the preparation of anti-freeze compositions and in the manufacture of polyester fibers. Various processes for the manufacture of ethylene glycol have been proposed, including those based upon the hydrolysis of ethylene oxide or the hydrolysis of carboxylate esters of ethylene glycol. U.S. Pat. No. 1,982,545, in the name of Skärblom, discloses the liquid-phase preparation of ethylene glycol directly from ethylene by reacting the ethylene with molecular oxygen in the presence of iodine or of a substance capable of readily liberating iodine under the conditions of the reaction. The overall reaction may be represented as follows:

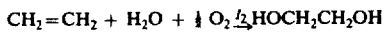

In the Skärblom process, the reaction takes place in a plurality of reaction chambers into which water and a mixture of ethylene and oxygen are introduced under superatmospheric pressure. The ethylene and oxygen are fed as a mixture in such a way that the aqueous reaction product which is produced is stripped in a final collecting zone of its more volatile components which are returned to the reaction by steam and the gas mixture and are thus recycled in toto to the reaction zones in which the glycol is being formed. More recently, Witheford U.S. Pat. No. 3,928,474 disclosed a variation of the Skärblom process in which the more volatile "light" components of the reaction mixture are separated by vacuum distillation and then wholly recycled to the first reaction zone. The ethylene glycol and high-boiling materials which are associated with it, on the other hand, are withdrawn completely from the reaction system in both the Skärblom and Witheford processes. In other words, all of the lower-boiling materials which are stripped from the product mixture by the incoming oxygen-ethylene mixture in the Skärblom process, or are separated from the reaction mixture by vacuum distillation in the Witheford process, are recycled to the reaction, whereas all other liquid materials are entirely withdrawn.

It has been observed that the above-described reaction involving ethylene, molecular oxygen and water in the presence of iodine produces not only glycol but also produces significant quantities of acetaldehyde, as well as substantial amounts of what can be characterized as polymeric or condensed forms of ethylene glycol, such as diethylene glycol, triethylene glycol, and the like. The acetaldehyde is apparently produced by the competing reaction

Although neither of the above-mentnioned patents refers to the co-production of acetaldehyde, Witheford does acknowledge the formation of poly-glycols in substantial amounts of the general order of at least 10% of the ethylene glycol even when the procedures of that patent are followed.

The continuous formation of poly-glycols represents a loss of selectivity to the desired monomeric ethylene glycol which is, of course, undesirable, and it has also been observed that, when acetaldehyde is totally recycled to the oxidation zone, as inherently occurs in the Skärblom and Witheford processes, it is converted into acetic acid which reacts with the monomeric glycol and the poly-glycols to form acetates which must later be treated to liberate the free hydroxyl compounds, complicating the recovery of the desired ethylene glycol.

It is accordingly an object of this invention to provide an improved process for the preparation of ethylene glycol by the molecular oxygen oxidation of ethylene in the presence of water and in the presence of iodine which avoids the disadvantages and drawbacks of the character indicated.

It is a further object of the invention to provide a process of the type described above wherein increased yields of purer forms of ethylene glycol are ensured.

It is a still further object of the invention to provide a process of the character indicated wherein the co-produced acetaldehyde can be effectively recovered as a valuable co-product.

Other objects and features of the invention will be readily apparent from the following detailed description of illustrative embodiments thereof and from the accompanying drawing which is a diagrammatic view in the nature of a flow sheet illustrating a representative embodiment of an apparatus assembly for carrying out the process of the invention.

In accordance with the invention, ethylene, water and molecular oxygen are reacted in the presence of iodine or an iodine-liberating compound in an oxidation zone in the liquid phase. The liquid reaction mixture is withdrawn from the oxidation zone and is separated into a light portion containing acetaldehyde, a heavy portion containing polymeric forms of ethylene glycol, and an ethylene glycol fraction. The ethylene glycol fraction is removed for purification, the light portion is treated to remove substantially all of its acetaldehyde content and the remainder of the light portion is returned to the oxidation zone. At the same time, the heavy portion is also recycled to the oxidation zone. It has been discovered that, surprisingly, the introduction of the separated glycol-polymer-containing heavy portion into the oxidation zone effectively suppresses the formation of additional glycol polymers in that zone so that once the initial quantity of polymeric material has been formed and its return by recycling to the oxidation zone has been initiated, as a continuous process, substantially all of the glycol moieties produced from the reactants subsequently fed into the oxidation zone are, in effect, obtained in the form of monomeric ethylene glycol and there is essentially no net gain of glycol polymers. It has also been discovered that by removing substantially all of the acetaldehyde before recycling the lighter components of the liquid phase reaction medium to the oxidation zone the reaction proceeds smoothly without adverse formation of acetic acid. There is thus obtained directly from the oxidation zone a monomeric ethylene glycol product in high yield which requires minimum purification.

The oxidation zone may be provided by a single reactor, such as an autoclave adapted to withstand the superatmospheric pressures under which the oxidation is carried out, or a plurality of reactors arranged in series may be employed, if desired. The liquid effluent from the oxidation zone is sent to one or more separation zones, e.g., distillation and/or evaporation zones, in which the above-mentioned light portion, heavy portion and ethylene glycol fraction are separated from each other. The oxidation zone into which the ethylene, oxygen, water and iodine or iodine-liberating compound are continuously charged, along with recycle components, is kept under a superatmospheric pressure sufficient to maintain the liquid phase. Ordinarily, a pressure in the range of 10 to 2000 psig, preferably 20 to 1000 psig, is employed although higher or lower pressures may be used depending upon the temperature as long as the liquid phase is maintained. Temperatures of the order of 50° to 250° C are generally suitable for the reaction but preferably the temperature is in the range of 75° to 200° C and most preferably a temperature of 100° to 180° C is employed. Ethylene, oxygen and water are added continuously to the reaction zone in which a catalytically-effective quantity of iodine or of an iodine-liberating compound is maintained. Various ratios of ethylene, oxygen and water can be employed. For example, the ratio of ethylene to oxygen can vary from 100:1 to 1:100 and the ratio of ethylene to water can vary from 10:1 to 1:100, all being molar ratios.

The iodine-liberating compound can be any compound capable of producing iodide ions in solution under the oxidation conditions. For example, the iodine-liberating compound can be an inorganic compound such as HI, or a metal iodide, such as $FeI_2$, $FeI_3$, $CrI_2$, $ZnI_2$, and like iodine compounds which hydrolyze to form HI, or it can be an organic iodine compound. In particular, the organic iodine compounds include all the iodine derivatives of the ethylene oxidized and of the reaction products. For example, in the oxidation of ethylene these include but are not limited to 1,2 diiodoethane, iodohydrin and other iodine containing derivatives of ethylene and including iodine derivatives of higher molecular weight ethers, and the like. Indeed, since many organic iodine compounds are formed in the course of the reaction and, in accordance with the invention, these iodine moieties are advantageously recycled to the oxidation zone so that the net supply of iodine to the system, once steady-state operation has been achieved, is at a minimum. In general, the quantity of iodine, expressed as HI, is in the range of about 0.1 to 20 wt. % of the liquid reaction mixture.

In the course of the continuous oxidation reaction, gaseous effluent composed primarily of unreacted oxygen, unreacted ethylene, carbon dioxide and carbon monoxide is continuously withdrawn and any condensible components in it are suitably returned to the reaction zone. If desired, unreacted ethylene and oxygen can be recycled to the reaction zone so that the fresh supply of oxygen and ethylene need be only that required to make up for the quantity of these reactants which have been consumed. The continuously removed portion of the liquid reaction mixture is composed primarily of ethylene glycol, water, polyglycols such as 1,4 dioxane, diethyleneglycol, and triethyleneglycol, iodo compounds such as iodohydrin, monoiododiethyleneglycol and monoiodotriethyleneglycol, and lower-boiling components such as acetaldehyde and, as mentioned, this liquid effluent is suitably separated into a plurality of portions or fractions. Thus, in a typical case, the liquid stream is supplied to a first separation zone which may advantageously take the form of one or more evaporators in which the lower-boiling components of the liquid stream are removed and, after suitable treatment to remove substantially all of the acetaldehyde that may be present and other by-products, the return of which to the oxidation zone may have an adverse effect upon the reaction, is recycled to the reaction zone. The non-vaporized portion of the liquid stream is then subjected to further separation, most suitably by fractional distillation or multi-stage evaporation, to provide a product fraction composed primarily of ethylene glycol, and a higher-boiling fraction containing some ethylene glycol and the polymeric forms of ethylene glycol which may be present in the liquid stream. The ethylene glycol fraction is in relatively pure form but may be subjected to further purification, if desired, by conventional means, e.g., fractional distillation, to increase its purity. In accordance with the invention, the higher-boiling fraction is recycled to the oxidation zone. A small purge of this fraction may be taken if desired in order to prevent the build up of undesirable high-boiling by-products. The conditions in the various separation zones can vary widely as will be understood by persons skilled in the art and the invention is in no way limited to any particular conditions.

Generally, however, the separation of the lower-boiling portion takes place at temperatures in the range of 90° to 200° C with pressures in the range of atmospheric to 400 psia and the separation of the product glycol fraction takes place at temperatures of 100° to 220° C and presures of 20 mm to 1 atmosphere, although these are only representative conditions and other temperatures and pressures may be employed, as will be apparent to persons skilled in the art. In any case, however, the higher-boiling fraction, which may be substantially free of monomeric glycol or which may contain some of the product glycol, e.g., up to about 50%, depending upon the sharpness of the separation between the product glycol and the higher-boiling fraction, is recycled to the oxidation zone and, as previously mentioned, it suppresses the formation of polymeric forms of ethylene glycol in the subsequent oxidation so that there is substantially no net formation of the polymeric ethylene glycol, and glycol moieties which are produced by reaction among the oxygen, ethylene and water are surprisingly obtained substantially entirely in the form of monomeric ethylene glycol.

It will be apparent that the process above described can be carried out in any conventional equipment which can readily be selected by persons skilled in the art, but the invention will be more fully understood by referring to the accompanying drawing which illustrates diagrammatically a typical apparatus arrangement for putting the process of the invention into practice. Referring then to the drawing, a reactor 10 provides an oxidation zone adapted to contain a liquid reaction mixture 12 and has an inlet conduit 14 for supplying ethylene, an inlet conduit 16 for admitting oxygen, and an inlet conduit 18 through which water is introduced into the reaction zone. The gaseous effluent from reactor 10 passes out via line 20 and through a condenser 22 to a separator 23 from which condensed components are returned to reactor 10 via line 24 and the noncondensible gases are removed via line 26. At the same time, the liquid effluent from the reaction zone is withdrawn through line 28 and passes to a first separation zone 30 wherein the lower-boiling constituents are removed through line 32 and, after separation of acetaldehyde, in recovery zone 34 and line 36, the remainder passes through conduit 38 into line 40 to be recycled to the oxidation zone. The heavier portion of the liquid reaction mixture entering recovery zone 30 is withdrawn through line 42 and passes to a second recovery zone 44 where, if present, remaining amounts of water are withdrawn through line 46 which communicates with line 40. The non-volatilized portion of the feed to separation zone 44 is withdrawn through line 48 and passes to a third separation zone 50 wherein the product glycol is separated as a distillate through line 52 and the higher-boiling portion of the feed is withdrawn through line 54 and, in accordance with the invention, is recycled to the oxidation zone through line 56, an optional purge being taken, if desired, through line 58. In the event all of the water and like lower-boiling materials have been separated from the liquid effluent in separation zone 30, separation zone 44 may be omitted and the material in line 42 may be fed directly into separation zone 50. In a typical preferred operation, reactor 10, as previously indicated, is operated at a temperature of 100° to 180° C under a pressure of 20 to 1000 psig. Ethylene, oxygen and water are supplied through lines 14, 16, and 18, respectively, advantageously in molar ratios to provide an ethylene to oxygen ratio of about 2:1 and an ethylene to water ratio of about 1:1. The flow of materials is adjusted to provide a residence time of about 0.5 to 10 hours in reactor 10.

In separation zone 30 temperatures of 100° to 180° C are preferably used and pressures ranging from atmospheric to 200 psia are preferably employed, and the acetaldehyde is separated from dissolved gases and dioxane in recovery zone 34, e.g., by fractional distillation or other means. Ordinarily, at least about 80% of the acetaldehyde is removed in recovery zone 34 before the remainder of the stream entering through line 32 is recycled to the reaction zone. Some or all of the dioxane may also be removed, if desired. Separation zone 44 is operated at a temperature of 90° to 200° C and under a pressure of 50 mm to 150 psig, and recovery zone 50 is operated at a temperature of 150° to 200° C and under a pressure of 20 mmHg to atmospheric.

It will be understood that the schematic representation of a reaction system shown in the drawing is for illustrative purposes only and that the invention is in no way limited to that embodiment. As previously indicated, each of the units illustrated, e.g., the oxidation zone, the recovery zone, and the separation zones may in practice consist of one or more vessels, e.g., autoclaves, evaporators, distillation columns, extraction devices, and the like.

The advantages and features of the invention will be more fully understood from the following example of typical operation of the process of the invention. This example, like the drawing, is being given for illustrative purposes only.

EXAMPLE

A one-gallon titanium autoclave equipped with a condenser is charged with 2720 gm. of $H_2O$ and 280 gm. of HI. The vessel is heated to 140° C., pressured to 450 psia with ethylene and 500 liters per hour of gas having a composition to 87% ethylene and 13% $O_2$ is passed through the vessel. After 6 hours, liquid is withdrawn at the rate of one liter per hour and passed to a distillation zone operated at 170° C and about 100 psia. About 25% of the feed is taken overhead in this zone and condensed first against cooling water and then in a dry ice trap. The combined condensate is treated for acetaldehyde removal by distillation at atmospheric pressure with a pot temperature of 90° C. About 5 gm./hr. of acetaldehyde are recovered and the remainder of the condensate is returned to the reaction zone.

The liquid effluent from the distillation zone (about 75% of the liquid withdrawn from the autoclave) is collected and batch dehydrated at 165° C. pot temperature. The head pressure is steadily reduced until it reaches about 85 mmHg. These overheads contain about 10% of the ethylene glycol product as well as recyclable iodine compounds, and are returned to the reactor. At the termination of distillation, about 200 cc of liquid remain in the pot.

An ethylene glycol product is recovered from this liquid by distillation at 170° C. and 45 mm overhead pressure. An average recovery of 95 gm./hr. is achieved.

Residue from the product distillation is returned to the reactor. It contains about 15 mol % ethylene glycol as well as recyclable digomers and iodine compounds. From time to time, water is added to the reactor to maintain liquid level. The average rate of water addition is about 30 gm./hr.

Analysis of the reaction mixture shows that the polyglycols (ethylene glycol dimers, oligomers, etc.) are essentially equilibrated in the system after only about 20 hours of continuous operation and the net make of such polyglycols at this point and in continued operation is essentially zero. Furthermore, the make of acetic acid is so low that it does not adversely influence the purity of the final glycol product even after 100 hours of continued operation.

What is claimed is:

1. A process for preparing ethylene glycol, which comprises reacting ethylene, molecular oxygen and water in the presence of an iodine source in an oxidation zone at a temperature of 50° - 250° C. and under a pressure sufficient to maintain the liquid phase to produce a liquid reaction product, separating said product into a plurality of portions, including a higher-boiling portion and a product ethylene glycol portion, and recycling said higher-boiling portion to said oxidation zone.

2. A process as defined in claim 1, wherein said portions include a lower-boiling portion and said lower-boiling portion is treated to remove acetaldehyde therefrom.

3. A process as defined in claim 2, wherein said lower-boiling portion after said treatment is recycled to said oxidation zone.

4. A process as defined in claim 1, wherein said portions include a lower-boiling portion, and said process further comprises treating said lower-boiling portion to remove acetaldehyde therefrom, recycling said lower-boiling portion to said oxidation zone, recovering said ethylene glycol as product, and recovering said acetaldehyde as co-product.

* * * * *